United States Patent [19]
Chalk et al.

[11] Patent Number: 5,118,837
[45] Date of Patent: Jun. 2, 1992

[54] SELECTIVE HYDROGENATION OF OLEFINS

[75] Inventors: Alan J. Chalk, Kinnelon; Laszlo V. Wertheimer, Woodbridge, both of N.J.

[73] Assignee: Givaudan Corporation, Clifton, N.J.

[21] Appl. No.: 13,608

[22] Filed: Feb. 12, 1987

[51] Int. Cl.⁵ ............... C07C 51/36; C07C 67/283; C07C 67/303; C07C 69/145

[52] U.S. Cl. .................. 560/261; 554/145; 544/178; 546/184; 560/265; 562/598; 568/687; 568/903; 585/273; 585/277

[58] Field of Search ............... 560/261, 265; 562/598; 585/273, 277; 568/903

[56] References Cited
U.S. PATENT DOCUMENTS 2,944,094  7/1960  Rylander et al.
3,452,105  6/1969  Marbet .................. 560/261

OTHER PUBLICATIONS

L. M. Berkowitz et al., J. Org. Chem. 24, (1959) 708–709.
J. Tsuji et al., Bull. Chem. Soc. Jap. 49, (1976) 1701–1702.
J. Tsuji et al., Chem. Lett. 1977 1083–1084.

Primary Examiner—Vivian Garner
Attorney, Agent, or Firm—Robert F. Tavares; Linda A. Vag

[57] ABSTRACT

A modified ruthenium catalyst can be used to selectively hydrogenate an olefinic double bond in the presence of another olefinic double bond in the same or in a different molecule. Modifiers are selected from compounds containing trivalent nitrogen, trivalent phosphorus and divalent sulfur.

8 Claims, 2 Drawing Sheets

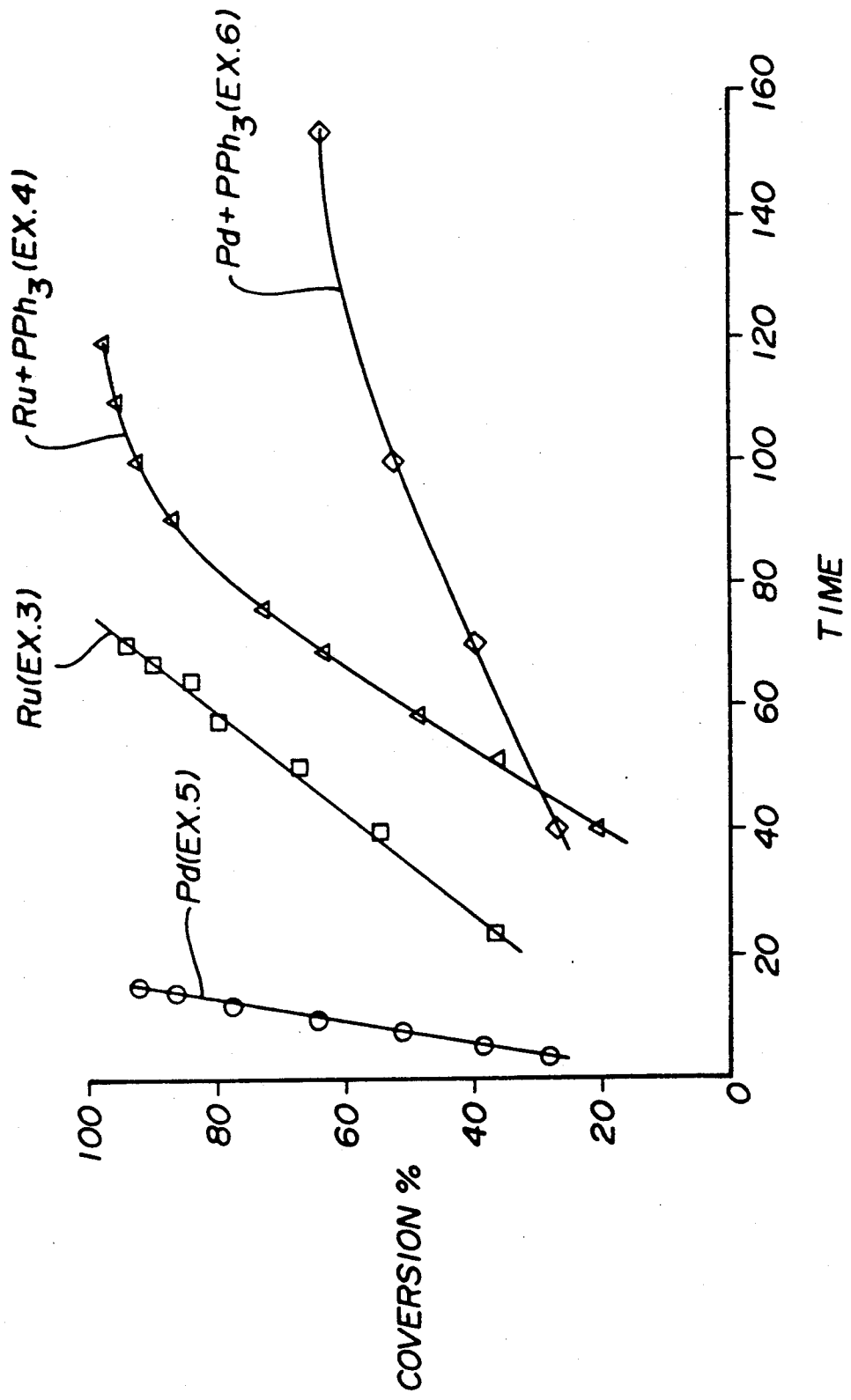

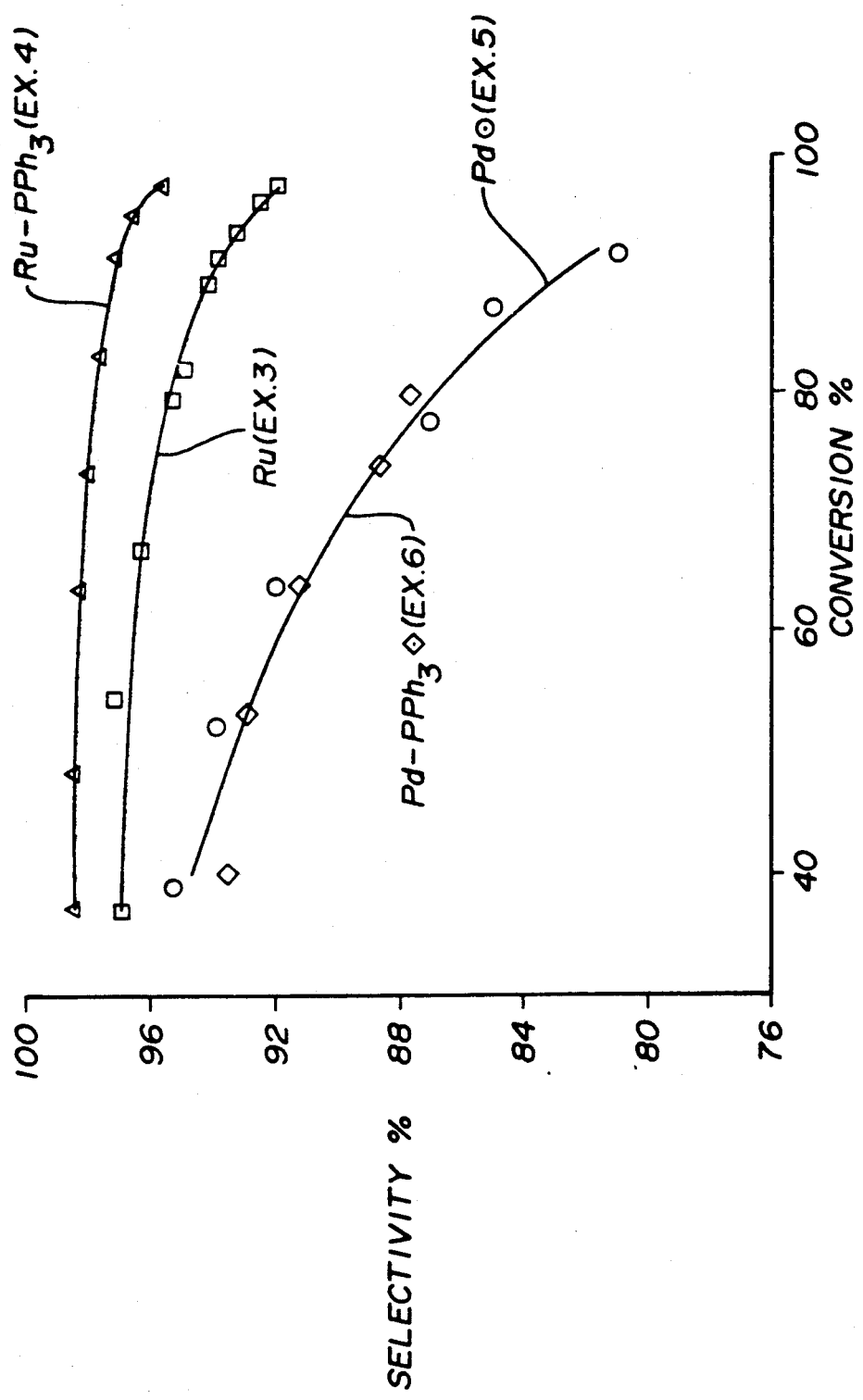

SELECTIVE HYDROGENATION OF OLEFINS

BACKGROUND OF THE INVENTION

Those practiced in the art of chemistry are often confronted with the problem of selectively hydrogenating one olefinic double bond in the presence of another olefinic double bond. Two cases are possible:
i) where the two olefinic double bonds are in the same molecule (intramolecular), and
ii) where the two olefinic double bonds are in separate molecules of a mixture (intermolecular).

Whenever the sites of two olefinic double bonds differ in some way such as the steric or electronic environment around the bond, a selective hydrogenation is theoretically possible. For example, the ease of hydrogenation of olefins is in the order: monosubstituted > disubstituted > trisubstituted > tetrasubstituted. It should be possible, in theory, to hydrogenate the less substituted olefinic double bond in the presence of the more substituted bond. In practice, however, very few catalysts have been found that allow for such selective hydrogenations. P. N. Rylander et al. disclosed ruthenium on carbon as a selective heterogeneous catalyst in the hydrogenation of simple hydrocarbon mixtures (case ii above) [J. Org. Chem. 24, 708 (1959); U.S. Pat. No. 2,944,094]. While mono-substituted olefins could be hydrogenated selectively in the presence of di- and trisubstituted olefins, no selectivity was observed when an attempt was made to hydrogenate disubstituted olefins in the presence of trisubstituted olefins.

Those practiced in the art are often faced with the problem presented in case (i) above, i.e., the selective hydrogenation of one of the two double bonds in a diene, especially in dienes having other functional groups. This case can be illustrated by Scheme I where it is desirable to obtain the substituted 2-octene II (reaction 1) relatively free of the octadiene, I, and the octane III (reaction 2). (The group X can represent a number of functional groups, e.g., OH, OCH$_3$, COOH, etc.)

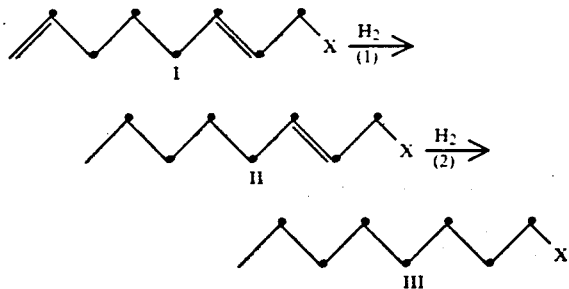

In such cases, it is important to achieve good selectivity for the formation of II at a high conversion of I because the boiling points of I, II and III are usually so similar that it is not commercially feasible to separate II from I and III by distillation. Thus, the purity of II obtained after distillation will essentially be whatever the purity of II is in the crude mixture of I, II and III.

There have been a number of attempts to improve the selectivity in Scheme I in favor of the olefin II, by converting I to II under conditions that favor the formation of II at high conversion of I, without at the same time converting II to III. All of these attempts dealt with the use of homogeneous catalyst systems. For example, Tsuji et al. [Bull. Chem. Soc. Japan, 49, 1701, (1976)] found that the homogeneous catalyst RhCl(PPh$_3$)$_3$ provided an 80% selectivity of II at 90% conversion of the octadiene I wherein X is an acetoxy group. This degree of selectivity, however, gives a product which is only about 72% pure. (For Scheme I, the purity of II can be calculated as the product of the selectivity of II times the conversion of I.) As has been suggested above, distillation will not provide a product where the content of II is increased because of the closeness of the boiling points. (The catalysts used by Tsuji et al. also suffer from the disadvantage that they are too slow unless pressures higher than 50 psi are used, e.g. 150-435 psi.)

The catalyst RuCl$_2$(PPh$_3$)$_3$, also a homogeneous catalyst, was reported to be selective [J. Tsuji & H. Suzuki, Chem. Lett. 1083, 1977] but no data was given. (We have found that this catalyst gives product mixtures with a purity of 63% to 64%. See Examples 1 and 2.)

While the prior art systems give good selectivity, the selectivity is not sufficient to provide purities of 90 to 100% of II. When purities of II of from 90% to 100% are required or desirable, they will only be achieved with use of a catalyst that will allow II to be prepared in high selectivity as the conversion of I approaches 100%.

THE INVENTION

This invention provides an improved process for the selective hydrogenation of one olefinic double bond in the presence of another olefinic double bond. The improved process utilizes a novel catalyst system comprising ruthenium, water and a modifier. The modifier can be any compound having a trivalent phosphorus, a trivalent nitrogen or a divalent sulfur. It has been found that addition of the modifier provides improved selectivity at higher conversions which results in products of higher purity. There is provided herein a number of examples which illustrate the surprising and unexpected results obtained in selective hydrogenations with this novel catalyst system.

The process and catalyst system of this invention can be used to improve selectivity whenever the two olefinic double bonds are different, e.g., monosubstituted olefinic double bonds can be hydrogenated in the presence of disubstituted olefinic double bonds and disubstituted olefinic double bonds can be hydrogenated in the presence of trisubstituted olefinic double bonds. This invention can also be used to improve selectivity in the hydrogenation of similarly substituted olefinic double bonds which differ in some steric aspect in proximity to the double bond. The two olefinic double bonds may be in the same molecule or in separate molecules.

BRIEF DESCRIPTION OF THE DRAWINGS

FIG. 1 is a graph of selected data reported in Tables 1 and 2 for Examples 3 through 6. The percent conversion of the substrate, 1-acetoxyocta-2,7-diene, is plotted against the reaction time.

FIG. 2 is also a graph of selected data reported in Tables 1 and 2. The percent selectivity of the formation of 1-acetoxyoct-2-ene is plotted against the percent conversion of the substrate.

The ruthenium catalyst used in this invention is a heterogeneous catalyst and the claims are to be understood as encompassing a heterogeneous catalyst only. The form of the ruthenium used is not critical and any of the usual forms employed for a heterogeneous system may be used, e.g. in the metallic state such as a sponge or as the finely divided metal or as some metal precursor such as a ruthenium oxide, hydroxide or carbonate which can be reduced to the metallic state by reaction with hydrogen, or the ruthenium metal or metal precursor may be supported on a suitable carrier such as carbon, alumina, kieselguhr, diatomaceous earth and the like. The ruthenium metal or metal precursor may be deposited on a suitable support by a conventional method such as hydrolysis of a soluble salt of ruthenium, said procedures being commonly known in the art. It is preferred to use ruthenium metal supported on a suitable carrier since this form of ruthenium is found to be more active and requires the use of less catalyst. The ratio of ruthenium to support is not critical and the ruthenium may range from about 0.1 percent to about 50 percent of the total weight of ruthenium and support. It is preferred to use 5 percent ruthenium this being the most economical.

The concentration range of catalyst, expressed as ruthenium weight percent of substrate treated, is in the range of about 0.001 to 1.0 percent. When the ruthenium is unsupported, it is preferred to use concentrations in the higher range of about 0.01 to 1.0 percent. If the ruthenium is supported, it is preferred to use concentrations in the lower range of about 0.001 to 0.1 percent with 0.01 to 0.1 percent being especially preferred.

The modifiers that can be used are any compounds that contain trivalent phosphorus, trivalent nitrogen or divalent sulfur and include, but are not limited to, phosphines, phosphites, amines, nitriles, sulfides, thioureas, and the like. (For the purposes of this invention it is understood that the modifier and the substrate to be reduced are separate molecules and that the modifier is not a functional group on the substrate to be selectively reduced.) The trivalent phosphorus modifiers are preferred over the trivalent nitrogen or divalent sulfur modifiers since they surprisingly and unexpectedly provide maximum selectivity for the most part without a significant reduction in rate of hydrogenation. Typical trivalent phosphorus modifiers are the organic phosphines and the organic phosphites. Suitable modifiers are trialkylphosphines in which the alkyl group contains from four to ten carbon atoms, triarylphosphines such as triphenylphosphine, trialkylphosphites such as those in which the alkyl group has from one to ten carbon atoms, and triarylphosphites such as triphenylphosphite. The term "alkyl group" is to be understood to include straight chain, branched chain and alicylic groups. Among the trialkylphosphines those having more bulky alkyl substituents are preferred over those having less bulky substituents since it has been found that they retard the rate less. Especially preferred among the trivalent phosphorus compounds are the organic phosphites and triphenylphosphine since they are the most economical and provide the best results. Typical trivalent nitrogen compounds are trialkylamines such as those in which the alkyl group has from one to ten carbon atoms. Typical divalent sulfur compounds are the organic sulfides containing aryl or aralkyl groups such as phenyl or benzyl.

The amount of modifier used can vary from about 0.1 to about 5000 times the amount of the ruthenium used. When the preferred phosphorus modifiers are used, the preferred range is from about 1.0 to 500 parts by weight of modifier per part of ruthenium used. It is especially preferred to use a phosphite or triphenylphosphine in a ratio of about 10 to 100 parts by weight for every part by weight of ruthenium used. For those modifiers such as divalent sulfur which have a tendency to slow the reaction rate significantly, lesser amounts of the modifier are preferably used.

The hydrogenation is performed in the presence of water which may be present in the range of about 1 to 99 percent by weight of the olefin substrate, preferably 10 to 50 percent by weight of the substrate.

A solvent may be used but is not necessary. The solvent may be a saturated or aromatic hydrocarbon or a more polar solvent such as an alcohol. A solvent may be used to dissolve solid substrates and can be used in any convenient amount for such a purpose.

The reaction temperature may be in the range of about 0° C. to 100° C. A preferred temperature range is about 10° C. to 60° C. with 20° C. to 35° C. being especially preferred.

Reaction pressure is not critical and may be in the range of subatmospheric to about 2000 psig. Hydrogenation is favored by an increase in pressure; however, good selectivity together with activity is generally obtained at relatively low pressures, i.e., between atmospheric and 200 psi with 20 to 60 psi being especially preferred.

ILLUSTRATION OF THE PREFERRED EMBODIMENTS

The following examples are provided to illustrate the preferred embodiments of the present invention and to illustrate its advantages over available alternatives. The examples should not be construed as providing any limitation on the claims.

Examples 1 and 2 employed a homogeneous catalyst which required pressures of 250 to 450 psi. For these two examples a 300 ml stainless steel autoclave was used at ambient temperature. For the remaining examples, heterogeneous catalysts were employed at pressures up to 50 psi for which a Parr Shaker was employed.

General conditions for the heterogeneous hydrogenations, examples 3 and following, were as follows:

Hydrogenations at the 0.10 mole substrate level or higher were carried out in a 500 ml Parr-shaker apparatus. Starting pressure was in all cases 50 psi. Hydrogenation was allowed to proceed to about 25 psi pressure at which point the system was pressurized again to 50 psi. Samples were taken at various times, either by interrupting the hydrogenation process or via a specially adapted septum. In all cases a good correlation was found between calculated hydrogen uptake, measured hydrogen uptake and the composition of the mixture.

Hydrogenations of 0.02 mole of substrate were carried out by placing substrate, catalyst and water into a conventional 20×150 mm test tube which then was inserted into a Parr-shaker bottle adapted to receive it securely.

GC analyses for all examples were carried out either on a Varian Aerograph ® Model 2700 instrument using packed columns (Carbowax ® 20M 10% on Chromosorb ® P 60–80 mesh, 3 m×3 mm i.d.) and equipped with a thermal conductivity detector and a Spectraphysics Minigrator ® or a Hewlett-Packard Model 5880A using capillary columns (Carbowax ® 20M, fused silica, 30 m).

To better illustrate the advantages of the present invention over the prior art, it is helpful to compare results in a quantitative manner. The terms selectivity, conversion and purity as used herein are defined as follows:

Selectivity, S, is a measure of the formation of the desired product as compared with the formation of all products.

Conversion, C, is a measure of the conversion of the substrate to all products.

Purity, P, is the amount of the desired product in the reaction mixture (i.e., substrate plus products) and, for case i as illustrated in Scheme I, it is the product of the selectivity, S, times the conversion, C.

EXAMPLES 1 TO 26

Examples 1 to 26 concern the product selectivity and product conversion in the catalytic hydrogenation of 1-acetoxyocta-2,7-diene (I) to 1-acetoxyoct-2-ene (II) and 1-acetoxyoctane (III). Where given, selectivity refers to the selectivity of formation of II, purity refers to the percentage of II in the product mixture and conversion refers to the conversion of I (i.e. formation of II plus III).

EXAMPLES 1 AND 2

These examples provide results obtained with a homogeneous catalyst, i.e., RuCl$_2$(PPh$_3$)$_3$. These results are provided as a comparison to those obtained using the catalyst system of this invention.

EXAMPLE 1

A mixture of 33.6 grams of 1-acetoxyocta-2,7-diene (I), 0.30 g RuCl$_2$(PPh$_3$)$_3$, 1.5 ml triethylamine and 120 ml ethanol was heated in a 300 ml stainless steel autoclave under a hydrogen pressure of 450 psi at 30° C. After three hours the rate of hydrogenation was greatly decreased and the pressure drop corresponded to approximately the theoretical amount (0.2 moles). The reaction was stopped, the catalyst filtered off and the crude product analyzed by GC to give 12.5% I, 63.7% 1-acetoxyoct-2-ene (II), and 23.6% 1-acetoxyoctane (III). This corresponds to a selectivity of 72.8% for the formation of II at a 87.5% conversion of I.

EXAMPLE 2

Example 1 was repeated at a pressure of 250 psi of hydrogen and was stopped after 22 hours.

An analysis of the products showed less conversion (73.8%) but greater selectivity (86.0%) than in Example 1. The purity of II was similar (63.2%). This example coupled with Example 1 illustrates how the selectivity drops off as more substrate is converted.

EXAMPLES 3 TO 7 (TABLES 1 AND 2)

Examples 3 and 4 (Table 1) show results for the hydrogenation of 1-acetoxyocta-2,7-diene (I) with ruthenium on carbon both with and without the modifier triphenylphosphine. In example 3, the purity of the product II rises to a maximum of about 89% at a conversion of 96% but does not significantly increase further. In the presence of the modifier however, a purity of 94% is obtainable (example 4). Corresponding results for palladium on carbon are shown in examples 5, 6 and 7 (Table 2). Much poorer values are obtained with palladium and the addition of modifiers is seen to be without beneficial effect (examples 6 and 7). The results reported in examples 3 through 6 for the conversion of I are plotted against time in FIG. 1 which shows that while the modifer has little effect on the rate of hydrogenation with ruthenium, the modifier greatly poisons the palladium catalyst, i.e. has a deterring effect on the rate and extent of hydrogenation. FIG. 2 depicts a plot of the corresponding values of conversion and selectivity. While the modifier clearly enhances the selectivity (at all conversions) for ruthenium, it does not affect the selectivity of the palladium catalyst. A further comparison can be made in terms of the purity of the product which is given for the highest conversions in Tables 1 and 2.

TABLE 1

Hydrogenation of 1-acetoxyocta-2,7-diene with Ru/C

| Example | Modifier | Time (mins.) | Conversion % | Selectivity % | Purity % |
|---|---|---|---|---|---|
| 3$^{(a)}$ | None | 24 | 37.0 | 97.0 | — |
| | | 40 | 54.6 | 97.2 | — |
| | | 50 | 67.0 | 96.4 | — |
| | | 57 | 79.8 | 95.4 | — |
| | | 59 | 82.6 | 95.1 | — |
| | | 61 | 82.8 | 95.0 | — |
| | | 64 | 84.3 | 94.7 | — |
| | | 66 | 90.1 | 94.2 | — |
| | | 67 | 91.7 | 94.1 | — |
| | | 68 | 92.3 | 94.0 | 86.8 |
| | | 70 | 93.7 | 93.5 | 87.6 |
| | | 71 | 95.0 | 92.8 | 88.2 |
| | | 72 | 96.4 | 92.5 | 89.2 |
| | | 73 | 97.1 | 92.1 | 89.4 |
| 4$^{(b)}$ | PPh$_3$ | 40 | 20.9 | 98.4 | — |
| | | 51 | 36.9 | 98.4 | — |
| | | 59 | 48.6 | 98.4 | — |
| | | 69 | 62.9 | 98.2 | — |
| | | 76 | 73.1 | 97.9 | — |
| | | 91 | 86.4 | 97.6 | 84.3 |
| | | 100 | 92.6 | 97.1 | 89.9 |
| | | 110 | 96.1 | 96.6 | 92.8 |
| | | 120 | 98.2 | 95.7 | 94.0 |

$^{(a)}$0.25 g 5% Ruthenium on carbon, 6 ml water and 16.8 g 1-acetoxyocta-2,7-diene (I) hydrogenated in a Parr Shaker bottle at 25° C. and 50 psi.
$^{(b)}$Identical to Example 3 with the addition of 0.600 g triphenylphosphine.

TABLE 2

Hydrogenation of 1-Acetoxyocta-2,7-diene with Pd/C

| Example | Modifier | Time (mins.) | Conversion % | Selectivity % | Purity % |
|---|---|---|---|---|---|
| 5$^{(a)}$ | None | 3 | 24.5 | 98.4 | — |
| | | 5 | 39.0 | 95.4 | — |
| | | 7 | 52.1 | 93.9 | — |
| | | 9 | 64.1 | 91.9 | — |
| | | 11 | 77.9 | 87.0 | 67.8 |
| | | 13 | 87.1 | 85.0 | 74.0 |
| | | 14 | 92.1 | 81.0 | 74.6 |
| 6$^{(b)}$ | PPh$_3$ | 40 | 27.0 | 94.8 | — |
| | | 70 | 39.8 | 93.7 | — |
| | | 100 | 53.0 | 93.0 | — |
| | | 154 | 64.0 | 91.4 | — |
| | | 266 | 74.0 | 88.6 | 65.6 |
| | | 436 | 80.1 | 87.6 | 70.2 |
| 7$^{(c)}$ | Et$_3$N | 20 | 24.7 | 87.4 | — |
| | | 35 | 40.5 | 83.0 | 33.6 |
| | | 45 | 54.8 | 78.6 | 43.1 |

$^{(a)}$8.4 g 1-Acetoxyocta-2,7-diene, 3 ml water, and 5% palladium on charcoal (50% wet, 0.12 g) hydrogenated in a Parr-shaker bottle at 25° C. and 50 psi.
$^{(b)}$Identical to example 5 with the addition of 0.300 g triphenylphosphine.
$^{(c)}$Identical to example 5 with the addition of 3.60 g triethylamine.

EXAMPLES 8 TO 13 (TABLE 3)

Examples 8 to 13 (Table 3) allow the comparison of the effect of modifiers on other metals thereby showing the unique advantages of ruthenium. Example 8 shows that rhodium on carbon gives less selectivity than ruthenium on carbon and example 9 shows that the selectivity for rhodium is not improved with triphenylphosphine. Examples 10 and 11 give similar data for platinum. Unmodified, platinum is far less selective than ruthenium. With modifier, the selectivity is greatly improved but is still only comparable to unmodified ruthenium. Examples 12 and 13 show that iridium on carbon is a poor, relatively unselective catalyst and the addition of triphenylphosphine acts as a poison without improving the selectivity.

TABLE 3

| | | Hydrogenation of 1-Acetoxyocta-2,7-diene | | | |
|---|---|---|---|---|---|
| Example | Catalyst | Modifier | Time (mins.) | Conversion % | Selectivity % | Purity % |
| 8(a) | Rh/C | None | 22 | 61.5 | 92.6 | 56.9 |
| | | | 25 | 74.9 | 89.1 | 66.7 |
| | | | 28 | 86.4 | 87.0 | 75.2 |
| 9(b) | Rh/C | PPh$_3$ | 21 | 61.0 | 92.2 | 56.2 |
| | | | 26 | 73.2 | 91.6 | 67.1 |
| | | | 30 | 85.2 | 89.9 | 76.6 |
| 10(c) | Pt/C | None | 22 | 65.1 | 92.2 | 60.0 |
| | | | 25 | 77.8 | 90.6 | 70.5 |
| | | | 28 | 88.6 | 88.2 | 78.1 |
| 11(d) | Pt/C | PPh$_3$ | 55 | 62.6 | 96.6 | 60.5 |
| | | | 82 | 79.8 | 96.3 | 76.8 |
| | | | 103 | 89.4 | 95.7 | 85.6 |
| 12(e) | Ir/C | None | 12(f) | 53.3 | 91.0 | 48.5 |
| 13(g) | Ir/C | PPh$_3$ | 20(f) | 15.2 | 92.8 | 14.1 |

(a) 8.4 g 1-Acetoxyocta-2,7-diene and 0.12 g 5% rhodium on carbon hydrogenated at 50 psi
(b) Identical to example 8 with the addition of 0.3 g PPh$_3$
(c) Identical to example 8 substituting 5% platinum on carbon for rhodium on carbon.
(d) Identical to example 10 with the addition of 0.30 g triphenylphosphine
(e) Identical to example 8 substituting iridium on carbon for rhodium on carbon.
(f) Time in hours
(g) Identical to example 12 with the addition of 0.30 g triphenylphosphine

EXAMPLES 14 TO 17 (TABLE 4)

Examples 14 to 17 show that the increase in selectivity found for ruthenium on carbon when modifiers are added is a phenomenon found with unsupported ruthenium metal (ruthenium black) and occurs also with ruthenium supported on other materials such as alumina.

TABLE 4

| | | Hydrogenation of 1-Acetoxyocta-2,7-diene | | | |
|---|---|---|---|---|---|
| Example | Catalyst | Modifier | Time (mins.) | Conversion % | Selectivity % | Purity % |
| 14(a) | Ru/Al$_2$O$_3$ | None | 144 | 43.6 | 93.8 | — |
| | | | 152 | 56.4 | 90.4 | — |
| | | | 172 | 64.7 | 87.8 | 56.8 |
| | | | 218 | 87.4 | 83.4 | 72.9 |
| 15(b) | Ru/Al$_2$O$_3$ | PPh$_3$ | 545 | 57.1 | 97.4 | — |
| | | | 623 | 84.9 | 96.6 | 82.0 |
| | | | 655 | 94.2 | 96.1 | 90.5 |
| | | | 670 | 96.4 | 95.5 | 92.1 |
| 16(c) | Ru | None | 60 | 39.7 | 97.2 | 38.6 |
| | | | 90 | 65.9 | 91.0 | 60.0 |
| | | | 120 | 84.4 | 91.1 | 76.9 |
| 17(d) | Ru | PPh$_3$ | 165 | 38.7 | 98.4 | 38.1 |
| | | | 204 | 58.7 | 98.5 | 57.8 |
| | | | 264 | 79.2 | 98.1 | 77.7 |
| | | | 300 | 87.9 | 98.1 | 86.2 |

(a) 0.24 g 5% Ruthenium on alumina (Ru/Al$_2$O$_3$), 6 ml water and 16.8 g acetoxyocta-2,7-diene hydrogenated in a Parr-shaker bottle at 50 psi
(b) Identical to example 14 with the addition of 2.3 mmole triphenylphosphine.
(c) 8.4 g 1-Acetoxyocta-2,7-diene, 6 ml water and 0.06 g ruthenium black.
(d) Identical to example 16 with 0.30 g triphenylphosphine.

EXAMPLES 18 TO 28 (TABLE 5)

Table 5 provides examples wherein a wide range of modifiers is utilized. When compared with Example 3 (see Table 1) where no modifier was used, it can be seen that the presence of these modifiers results in significant improvements in selectivity. The effectiveness of the modifiers in increasing selectivity is in the approximate order.

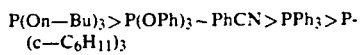

P(On—Bu)$_3$ > P(OPh)$_3$ ~ PhCN > PPh$_3$ > P-(c—C$_6$H$_{11}$)$_3$

Modifiers also caused a decrease in the rate of hydrogenation and this effect is in the approximate order:

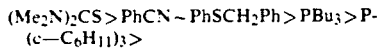

(Me$_2$N)$_2$CS > PhCN ~ PhSCH$_2$Ph > PBu$_3$ > P-(c—C$_6$H$_{11}$)$_3$ >

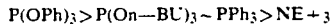

P(OPh)$_3$ > P(On—Bu)$_3$ ~ PPh$_3$ > NEt$_3$

Since the order is different in the two series, there are particular advantages in using modifiers which are high in the first series but not in the second, e.g. tributylphosphite. Sulfur compounds are highest in the second series, i.e. they behave as strong poisons. For this reason they were used at very low levels. Even at 1 millimole of modifier per gram of 5% ruthenium on charcoal, tetramethylthiourea completely deactivated the catalyst. Use of phenyl benzyl sulfide at this level gave a selective hydrogenation however. Using a tenfold increase of modifier, benzonitrile caused a very sluggish catalysis. Prehydrogenating the catalyst increased the rate of hydrogenation and gave a selective hydrogenation. Since benzonitrile was found to be slowly hydrogenated however, it is not a good modifier.

Examples 18 to 28 were carried out in a manner identical to example 3 except that the amounts were halved (8.4 g 1-acetoxyocta-2,7-diene, 3 ml water and 0.12 g 5% ruthenium on carbon) and in addition, a modifier was added in the amount shown in Table 5. In each case the modifier was dissolved in 15 ml ethanol except for examples 22 and 25 where the ethanol was omitted. In example 22 which employed benzonitrile, the catalyst was preactivated by shaking with the water and hydrogen for 1.5 hours before adding substrate and modifier. Conversion of 1, selectivity of 11 and purity of 11 were calculated as in examples 1 to 17.

TABLE 5

| | Hydrogenation of 1-acetoxyocta-2,7-diene | | | | |
|---|---|---|---|---|---|
| | Effect of Various Modifiers | | | | |
| Example | Modifier | (mmole) | Time Hours | Conversion % | Selectivity % | Purity % |
| 18 | P(On-Bu)$_3$ | 1.15 | 1.5 | 98.9 | 98.4 | 97.3 |
| 19 | P(OEt)$_3$ | 1.15 | 43 | 86.3 | 99.3 | 85.7 |
| 20 | P(OPh)$_3$ | 1.15 | 4 | 92.3 | 98.8 | 91.2 |
| 21 | P(OPh)$_3$ | 0.39 | 3 | 98.7 | 97.7 | 96.4 |
| 22 | PhCN | 1.2 | 16.3 | 97.6 | 97.3 | 95.0 |
| 23 | NEt$_3$ | 14 | 0.38 | 94.2 | 96.8 | 91.2 |
| 24 | NBu$_3$ | 14 | 8 | 97.2 | 97.1 | 94.5 |
| 25 | PhSCH$_2$Ph | 0.115 | 4 | 92.3 | 96.3 | 88.9 |
| 26 | Ph$_2$S | 0.230 | 8.5 | 88.5 | 95.5 | 84.5 |
| 27 | P(c-C$_6$H$_{11}$)$_3$ | 1.15 | 3.5 | 98.9 | 90.5 | 89.5 |
| 28 | P(n-Bu)$_3$ | 1.15 | 7 | 47.8 | 100 | 47.8 |

EXAMPLES 29 TO 40 (TABLE 6)

These examples illustrate how $H_2C=CH-(CH_2)_3-CH=CH-CH_2-X$ can be selectively reduced to $H_3C-CH_2-(CH_2)_3-CH=CH-CH_2-X$ wherein X is a substituent which is varied.

In the absence of modifier the selectivity of these reactions varies from very high (X=N-morpholino) to only moderate (X=COOMe). In the former case it appears that the N-morpholino group is acting as its own modifier. Thus morpholine is a better modifier than most other amines and even improves the selectivity of the N-piperidino derivative (example 37). In all other cases the selectivity is greatly improved by the addition of a phosphorus modifier such as tributylphosphite or triphenylphosphine.

The procedure in all these examples was identical to example 3 except the substrate was changed as indicated in Table 6 (variation of X). In each case 50 mmole of substrate were employed which is half the amount of substrate used in example 3. For this reason, the amounts of catalyst and water were halved correspondingly. When a modifier was also employed, the amount is also shown in Table 6. The conversion refers in each case to the conversion of the substrate indicated, the selectivity refers to the selectivity of the desired product $[CH_3(CH_2)_4CH=CHCH_2X]$ and the purity refers to the percent of the desired product in the product mixture.

TABLE 6

Hydrogenation of $CH_2=CH(CH_2)_3CH=CHCH_2X$[a]

| Example | X | Modifier | Time Hours | Conversion % | Selectivity % | Purity % |
|---|---|---|---|---|---|---|
| 29[b] | N-morpholino | None | 7.0 | 96.2 | 96.7 | 93.0 |
| 30 | COOH | None | 3.5 | 95.1 | 92.4 | 87.9 |
| 31 | COOH | PPh$_3$ | 6.2 | 97.1 | 94.5 | 91.8 |
| 32 | OH | None | 13.0 | 97.4 | 85.6 | 83.4 |
| 33 | OH | PPh$_3$ | 22.0 | 97.1 | 95.4 | 92.6 |
| 34[b] | OMe | None | 1.0 | 92.9 | 91.5 | 85.0 |
| 35[b] | OMe | P(On-Bu)$_3$ | 6.0 | 98.7 | 97.6 | 96.3 |
| 36 | N-piperidino | None | 7.0 | 94.0 | 90.2 | 84.8 |
| 37[c] | N-piperidino | Morpholine | 10.0 | 94.7 | 93.1 | 88.2 |
| 38 | N-piperidino | PPh$_3$ | 11.6 | 94.4 | 97.8 | 92.3 |
| 39 | COOMe | None | 3.5 | 94.6 | 83.0 | 78.5 |
| 40 | COOMe | PPh$_3$ | 3.8 | 98.4 | 94.1 | 92.6 |

[a] 50 mmole substrate, 120 mg Ru/C, 3 ml H$_2$O and 1.2 m mole moderator except for examples 39 and 40 in which all quantities were reduced to one-fifth of the above.
[b] 15 ml EtOH additional.
[c] 12 mmole morpholine used.

EXAMPLES 41 AND 42 (TABLE 7)

The examples to this point are all of the type $CH_2=CH(CH_2)_3CH=CH(CH_2)_nX$ where n=1. Examples 41 and 42 show that when n=2 the presence of a modifier similarly results in an improvement in selectivity and purity. Table 7 gives the results obtained in the hydrogenation of 1-acetoxynona-3,8-diene to 1-acetoxynon-3-ene and 1-acetoxynonane.

TABLE 7

Hydrogenation of 1-Acetoxynona-3,8-diene

| Example | Modifier | Time (hrs.) | Conversion of 1-acetoxynona-3,8-diene % | Selectivity for 1-acetoxynon-3-ene % | Purity of 1-acetoxynon-3-ene % |
|---|---|---|---|---|---|
| 41[a] | None | 2.00 | 55.3 | 97.1 | — |
|  |  | 2.92 | 77.0 | 96.6 | — |
|  |  | 3.75 | 91.4 | 95.7 | 87.5 |
|  |  | 3.92 | 94.2 | 93.7 | 88.3 |
|  |  | 4.25 | 97.3 | 92.7 | 90.2 |
| 42[b] | PPh$_3$ | 4.25 | 64.1 | 99.1 | — |
|  |  | 5.45 | 80.0 | 98.9 | 79.1 |
|  |  | 9.00 | 99.8 | 97.7 | 97.5 |

[a] 2.7 g 1-Acetoxynona-3,8-diene, 0.036 g 5% ruthenium on carbon and 0.9 ml water.
[b] Identical to example 41 with the addition of 0.09 g triphenylphosphine.

EXAMPLES 43 TO 46 (TABLES 8 AND 9)

To this point, the examples have concerned the catalyst selectivity between double bonds having different numbers of vinyl hydrogens. Examples 43 to 46 show that improved selectivity is possible even when the number of vinyl hydrogens is the same. Table 8 gives the results obtained in the hydrogenation of 3-acetoxyocta-1,7-diene to 3-acetoxyoctene and 3-acetoxyoctane. Table 9 gives the results obtained in the hydrogenation of 1,9-decadiene to 1-decene and decane.

TABLE 8

Hydrogenation of 3-Acetoxyocta-1,7-diene

| Example | Modifier | Time (mins.) | Conversion of 3-acetoxyocta-1,7-diene % | Selectivity for 3-acetoxyoctene % | Purity of 3-acetoxyoctene % |
|---|---|---|---|---|---|
| 43[a] | None | 144 | 41.0 | 88.5 | — |
|  |  | 274 | 69.8 | 78.5 | 54.8 |
|  |  | 340 | 78.9 | 75.7 | 59.7 |

TABLE 8-continued

| | | | Hydrogenation of 3-Acetoxyocta-1,7-diene | | |
|---|---|---|---|---|---|
| Example | Modifier | Time (mins.) | Conversion of 3-acetoxyocta-1,7-diene % | Selectivity for 3-acetoxyoctene % | Purity of 3-acetoxyoctene % |
| 44(b) | PPh₃ | 370 | 47.6 | 91.0 | — |
| | | 550 | 75.4 | 87.3 | 65.8 |
| | | 760 | 88.1 | 83.5 | 73.6 |

(a) 4 g 3-Acetoxyocta-1,7-diene hydrogenated in the presence of 0.12 g ruthenium on carbon and 3 ml water
(b) Identical to example 43 with the addition of 0.30 g triphenylphosphine.

TABLE 9

| | | | Hydrogenation of 1,9-Decadiene | | |
|---|---|---|---|---|---|
| Example | Modifier | Time (hrs.) | Conversion of 1,9-decadiene % | Selectivity for 1-decene % | Purity of 1-decene % |
| 45(a) | None | 2.50 | 44.5 | 63.8 | 28.4 |
| | | 4.05 | 56.4 | 62.0 | 35.0 |
| | | 6.17 | 61.8 | 61.2 | 37.8 |
| 46(b) | PPh₃ | 2.87 | 43.4 | 72.6 | 31.5 |
| | | 3.28 | 58.2 | 67.4 | 39.2 |
| | | 4.33 | 66.7 | 62.8 | 41.9 |

(a) 6 g 1,9-Decadiene, 3 ml water and 0.12 g 5% ruthenium on carbon were hydrogenated at 50 psi.
(b) Identical to example 45 with the addition of 0.3 g triphenylphosphine.

EXAMPLES 47 TO 50 (TABLES 10 AND 11)

Examples 47 to 50 are further examples of the intramolecular case for simple hydrocarbons. In all cases, a substantial increase in selectivity was found by adding modifiers such as triphenylphosphine. Examples 47 and 48 (Table 10) illustrate the hydrogenation of 2,6-dimethylocta-2,7-diene to 2,6-dimethyl-2-octene and 2,6-dimethyloctane. Examples 49 and 50 (Table 11) illustrate the hydrogenation of 1-vinyl-3-cyclohexene to 1-ethyl-3-cyclohexene and 1-ethyl-cyclohexane.

TABLE 10

| | | | Hydrogenation of 2,6-Dimethylocta-2,7-diene | | |
|---|---|---|---|---|---|
| Example | Modifier | Time (mins.) | Conversion of 2,6-dimethylocta-2,7-diene % | Selectivity for 2,6-dimethyl-2-octene % | Purity of 2,6-dimethyl-2-octene % |
| 47(a) | None | 20 | 64.3 | 96.9 | 62.3 |
| | | 30 | 88.3 | 94.3 | 83.3 |
| 48(b) | PPh₃ | 80 | 97.4 | 95.6 | 93.1 |

(a) 1.4 g 2,6-Dimethylocta-2,7-diene, (VII), 0.04 g 5% ruthenium on carbon and 0.9 ml water hydrogenated at 50 psi
(b) Identical to example 47 with the addition of 0.075 g triphenylphosphine.

TABLE 11

| | | | Hydrogenation of 1-Vinyl-3-cyclohexene | | |
|---|---|---|---|---|---|
| Example | Modifier | Time (mins.) | Conversion of 1-vinyl-3-cyclohexene % | Selectivity for 1-ethyl-3-cyclohexene % | Purity of 1-ethyl-3-cyclohexene % |
| 49(a) | None | 40 | 47.2 | 85.6 | — |
| | | 76 | 89.7 | 77.0 | 69.1 |
| | | 90 | 97.1 | 72.2 | 70.1 |
| 50(b) | PPh₃ | 82 | 77.8 | 87.8 | 68.3 |
| | | 113 | 92.3 | 84.4 | 77.9 |

(a) 9 g 1-Vinyl-3-cyclohexene 0.5 g 5% ruthenium on carbon and 7.5 ml water hydrogenated at 50 psi.
(b) Identical to example 49 with the addition of 1.0 g triphenylphosphine.

EXAMPLES 51 TO 54 (TABLES 12 AND 13)

Examples 51 to 54 show that the effect of modifiers is not limited to the intramolecular case for hydrocarbons but are also of value in the hydrogenation of hydrocarbon mixtures. (case ii) where it is desirable to hydrogenate a less substituted double bond in the presence of a more substituted double bond.

Examples 51 and 52 (Table 12) illustrate the hydrogenation of a simple olefin mixture, namely the hydrogenation of 2-octene to octane in the presence of 2,6-dimethyloct-2-ene. Examples 53 and 54 (Table 13) illustrate the hydrogenation of a mixture of olefins bearing polar substituents, namely the hydrogenation of 1-acetoxyundec-10-ene to undecylacetate in the presence of 1-acetoxydec-4-ene.

TABLE 12

| | | Hydrogenation of a Mixture of 2-Octene and 2,6-Dimethyloct-2-ene | | |
|---|---|---|---|---|
| Example | Modifier | Time(a) Hours | Conversion of 2-Octene % | Selectivity for Octane % |
| 51(a) | None | 6.77 | 37.0 | 91.1 |
| | | 6.90 | 53.3 | 91.6 |
| | | 7.10 | 76.4 | 91.4 |
| | | 7.17 | 85.8 | 90.4 |
| | | 7.24 | 93.5 | 88.5 |
| | | 7.29 | 97.7 | 86.3 |
| 52(c) | PPh₃ | 3.30 | 40.2 | 98.0 |
| | | 4.80 | 59.7 | 98.3 |
| | | 7.30 | 83.6 | 97.5 |

TABLE 12-continued

Hydrogenation of a Mixture of 2-Octene and 2,6-Dimethyloct-2-ene

| Example | Modifier | Time(a) Hours | Conversion of 2-Octene % | Selectivity for Octane % |
|---|---|---|---|---|
| | | 8.00 | 91.6 | 96.8 |
| | | 8.60 | 93.9 | 96.4 |
| | | 9.20 | 96.6 | 95.7 |

(a)Time is measured from the start of the reaction and includes an induction period of about 6 hours
(b)A mixture of 2.62 g (23 mmole) 2-octene, 3.21 g (23 mmole) 2,6-dimethyloct-2-ene, 2.6 ml water and 0.20 g 5% ruthenium on carbon hydrogenated at 50 psi in a Parr Shaker hydrogenator.
(c)Identical to example 51 with the addition of 0.3 g triphenylphosphine

TABLE 13

Hydrogenation of a Mixture of 1-Acetoxydec-4-ene and 1-Acetoxyundec-10-ene

| Example | Modifier | Time (mins.) | Conversion of 1-Acetoxyundec-10-ene % | Selectivity for Undecylacetate % |
|---|---|---|---|---|
| 53(a) | None | 330 | 46.2 | 97.5 |
| | | 500 | 71.9 | 96.9 |
| | | 770 | 85.4 | 95.7 |
| 54(b) | PPh$_3$ | 583 | 46.0 | 98.3 |
| | | 918 | 71.5 | 98.6 |
| | | 1500 | 95.0 | 97.2 |

(a)50 mmole of 1-acetoxydec-4-ene and 50 mmole 1-acetoxyundec-10-ene hydrogenated in the presence of 0.24 g ruthenium on carbon and 6 ml water at 50 psi.
(b)Identical to example 53 with the addition of 0.60 g triphenylphosphine

We claim:

1. A process for the selective hydrogenation of an olefinic double bond in the presence of other, less reactive olefinic double bonds wherein the olefinic double bond to be hydrogenated and the other less reactive olefinic double bonds may be in the same molecule or different molecules, which comprises:
  a) subjecting an organic substrate having said olefinic double bond to be hydrogenated to hydrogen gas in the presence of a heterogeneous ruthenium catalyst, water and a modifier, said modifier being
    i) a trivalent phosphorus compound selected from the group consisting of trialkylphosphines, triarylphosphines, trialkylphosphites and triarylphosphites;
    ii) a trivalent nitrogen compound selected from the group consisting of trialkylamines; or,
    iii) a divalent sulfur compound selected from the group consisting of organic sulfides containing aryl or aralkyl groups, and,
  b) hydrogenating at a temperature from about 0° C. to about 100° C., and, at a pressure from subatmospheric to about 2000 psig, until an amount of hydrogen gas has been absorbed which is sufficient to hydrogenate said olefinic double bond to be hydrogenated.

2. The process according to claim 1 wherein the ruthenium is in the metallic state or is in the form of a metal precursor, or is a deposit on a suitable carrier system selected from the group consisting of carbon, alumina, kieselguhr and diatomaceous earth.

3. The process according to claim 2 wherein:
  a) the modifier is present in an amount from about 0.1 to about 5000 times the amount of ruthenium present,
  b) the ruthenium is present in an amount from about 0.001 percent to about 1.0 percent of the amount of the organic substrate present, and,
  c) the water is present in an amount from about 1 percent to 99 percent of the amount of the organic substrate present.

4. The process according to claim 3, wherein:
  a) the trialkylphosphine contains straight chain, branched chain or cyclic alkyl groups having from four to ten carbon atoms;
  b) the triarylphosphine is triphenylphosphine;
  c) the trialkylphosphite contains straight chain, branched chain or cyclic alkyl groups having from one to ten carbon atoms;
  d) the triarylphosphite is triphenylphosphite;
  e) the trialkylamine contains alkyl groups having from one to ten carbon atoms; and,
  f) the organic sulfide contains phenyl or benzyl groups.

5. The process according to claim 4 wherein:
  a) the ruthenium is a deposit on carbon or on alumina, and,
  b) the modifier is a trivalent phosphorus compound.

6. The process according to claim 5 wherein:
  a) the trivalent phosphorus compound is present in an amount from about 1.0 to about 500 times the amount of ruthenium present;
  b) the ruthenium is present in an amount from about 0.001 percent to about 0.1 percent of the amount of the organic substrate present;
  c) the water is present in an amount from about 10 percent to about 50 percent of the amount of the organic substrate present;
  d) the temperature is from about 10° C. to about 60° C.; and,
  e) the pressure is from atmospheric to about 200 psi.

7. The process according to claim 6 wherein:
  a) the ruthenium is a deposit on carbon;
  b) the trivalent phosphorus compound is selected from the group consisting of triphenylphosphine, triphenylphosphite and trialkylphosphites containing straight chain, branched chain or cyclic alkyl groups having from one to ten carbon atoms;
  c) the ruthenium is from about 0.1 percent to about 50 percent of the total weight of the metal and the carbon;
  d) the ruthenium is present in an amount of from about 0.01 percent to about 0.1 percent of the amount of the organic substrate present;
  e) the trivalent phosphorus compound is present in an amount from about 10 to about 100 times the amount of ruthenium present;
  f) the temperature is from about 20° C. to about 35° C.; and,
  g) the pressure is from about 20 psi to about 60 psi.

8. The process according to claim 7, wherein 1-acetoxyocta-2,7-diene is selectively hydrogenated to 1-acetoxyoct-2-ene.

* * * * *